(12) United States Patent
Yamauchi

(10) Patent No.: US 6,819,422 B2
(45) Date of Patent: Nov. 16, 2004

(54) MEASURING METHOD FOR IMMUNOCHROMATOGRAPHIC TEST STRIP

(75) Inventor: Kazunori Yamauchi, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 0 days.

(21) Appl. No.: 10/257,440

(22) PCT Filed: Apr. 6, 2001

(86) PCT No.: PCT/JP01/02990

§ 371 (c)(1),
(2), (4) Date: Oct. 11, 2002

(87) PCT Pub. No.: WO01/77679

PCT Pub. Date: Oct. 18, 2001

(65) Prior Publication Data

US 2003/0098976 A1 May 29, 2003

(30) Foreign Application Priority Data

Apr. 12, 2000 (JP) ........................ 2000-111144

(51) Int. Cl.⁷ ............................................ G01N 21/00
(52) U.S. Cl. ...................................................... 356/344
(58) Field of Search ................................. 356/344, 326, 356/346, 318, 319, 72

(56) References Cited

U.S. PATENT DOCUMENTS

| | | | | |
|---|---|---|---|---|
| 4,537,861 A | * | 8/1985 | Elings et al. | ................ 436/518 |
| 5,313,264 A | * | 5/1994 | Ivarsson et al. | ............... 356/73 |
| 5,480,775 A | * | 1/1996 | Ito et al. | ....................... 435/7.2 |
| 5,770,389 A | * | 6/1998 | Ching et al. | ................ 435/7.92 |
| 6,134,002 A | * | 10/2000 | Stimson et al. | ............. 356/326 |
| 6,245,507 B1 | * | 6/2001 | Bogdanov | ........................ 435/6 |

FOREIGN PATENT DOCUMENTS

| | | |
|---|---|---|
| JP | 61-262635 | 11/1986 |
| JP | 5-45332 | 2/1993 |
| JP | 5-52809 | 3/1993 |
| JP | 7-5110 | 1/1995 |
| JP | 8-334511 | 12/1996 |
| JP | 2000-121562 | 4/2000 |
| WO | WO 95/13531 | 5/1995 |

* cited by examiner

*Primary Examiner*—Michael P. Stafira
(74) *Attorney, Agent, or Firm*—Morgan, Lewis & Bockius LLP (57) ABSTRACT

A measuring device comprises an irradiation optical system and a detection optical system. The irradiation optical system comprises a light-emitting element. The detection optical system comprises a cylindrical lens and an imaging element. The cylindrical lens is disposed in such a manner that the direction of a generating line thereof intersects with the direction of travel of the antigens or antibodies in an immunochromatography teat piece. The cylindrical lens creates an image of a pattern formed so as to extend in a direction intersecting with the direction of travel of the antigens or antibodies, on the imaging element. The imaging element detects the image formed by the cylindrical lens.

8 Claims, 8 Drawing Sheets

MEASURING METHOD FOR IMMUNOCHROMATOGRAPHIC TEST STRIP

TECHNICAL FIELD

The present invention relates to a device for measuring immunochromatography test pieces.

BACKGROUND ART

In immunochromatography analysis, antibodies (or antigens) which provoke a antigen or antibody reaction with antigens (or antibodies) in a subject (sample) are previously coated in strips onto prescribed positions of an immunochromatography test piece. After applying a subject to an immunochromatography test piece, the antigens (or antibodies) in the subject are dissolved out using a developer solution, and are caused to impregnate into the immunochromatography test piece, whereupon the antigens (or antibodies) in the subject are trapped by an antigen or antibody reaction in the region of the antigens (or antibodies) coated onto the immunochromatography test piece. Since the quantity trapped is the total amount of that antigen (or antibody) in the subject, it is possible to measure the total amount of the antigen (or antibody) by means of optical measurement, such as light absorption, or the like, if the antigen (or antibody) in the subject is previously marked by a dye. Immunochromatography analysis can be used for measuring extremely small quantities, compared to standard colorimetric methods.

Japanese Patent Laid-open No. H7-5110 discloses a measuring device for measuring the concentration of a specific material in a subject from an immunochromatography test piece after development and dying of the subject. In the measuring device described in Japanese Patent Laid-open No. H7-5110, light from an LED is irradiated onto an immunochromatography test piece, the light reflected from the immunochromatography test piece is detected by a CCD color image sensor, and the degree of coloration is identified.

DISCLOSURE OF THE INVENTION

In an immunochromatography test piece, the portion which is colored by the antigen or antibody reaction extends in a direction which intersects with the path of movement of the subject, and cases are observed wherein uneven coloring occurs in the direction in which the colored portion extends. If uneven coloring occurs in the colored portion in this way, then it becomes difficult to measure the degree of coloring with good accuracy.

The present invention was devised with the foregoing in view, an object thereof being to provide a measuring device for immunochromatography test pieces which is capable of measuring the degree of coloring of immunochromatography test pieces to a high level of accuracy.

In order to achieve the aforementioned object, the measuring device for immunochromatography test pieces according to the present invention is a measuring device for immunochromatography test pieces, comprising an irradiation optical system for irradiating measurement light onto immunochromatography test pieces; and a detection optical system for detecting light from the immunochromatography test pieces due to the measurement light; characterized in that the detection optical system comprises a cylindrical lens and an imaging element; and the cylindrical lens is disposed in such a manner that the direction of the generating line thereof intersects with the direction of travel of antigens or antibodies in the immunochromatography test piece, and creates an image of a pattern formed in a direction intersecting with the direction of travel of the antigens or antibodies, on the imaging element, due to the irradiation of the measurement light from the irradiation optical system.

The detection optical system has a cylindrical lens and an imaging element, and in particular, the cylindrical lens is disposed in such a manner that the direction of the generating line thereof intersects with the direction of travel of antigens or antibodies in the immunochromatography test piece, and creates an image of a pattern formed in a direction intersecting with the direction of travel of the antigens or antibodies, on the imaging element, due to the irradiation of the measurement light from the irradiation optical system. Therefore, light that is parallel to the direction of travel of the antigens or antibodies in the immunochromatography test piece is formed as an image on the imaging element, and light that is orthogonal to the direction of travel of the antigens or antibodies in the immunochromatography test piece is defocused and equalized. Consequently, even if there is unevenness in the coloration in the direction of extension of the colored region, then the uneven coloration is optically equalized by the cylindrical lens, and a pattern wherein uneven coloration is optically equalized is formed as an image on the imaging element. As a result, it is possible to measure the degree of coloration of the immunochromatography test piece with a high level of accuracy.

The measuring device for immunochromatography test pieces according to the present invention may be further characterized in that a member formed with a slit extending in the direction of the generating line of the cylindrical lens is further provided between the immunochromatography test piece and the cylindrical lens.

By providing a member formed with a slit extending in the direction of the generating line of the cylindrical lens between the immunochromatography test piece and the cylindrical lens, it is possible to form an image having little aberration on the imaging element.

Moreover, the measuring device for immunochromatography test pieces according to the present invention may be further characterized in that the imaging element is a linear image sensor wherein a plurality of light-receiving elements are arrayed in a direction approximately orthogonal to the direction of the generating line of the cylindrical lens.

By using a linear image sensor wherein a plurality of light-receiving elements are arrayed in a direction approximately orthogonal to the direction of the generating line of the cylindrical lens, it is possible to realize a measuring device having an inexpensive and compact composition. As described above, since the uneven coloration is optically equalized by the cylindrical lens, then the degree of coloration of the immunochromatography test piece can be measured with good accuracy, even if a linear image sensor is used as the imaging element.

Furthermore, the measuring device for immunochromatography test pieces according to the present invention may be further characterized in that the irradiation optical system and the detection optical system are disposed in such a manner that the imaging element receives the transmitted light of the measurement light irradiated onto the immunochromatography test piece; and the light absorption of the color pattern is measured on the basis of the transmitted light received by the imaging element.

The degree of coloration of the immunochromatography test piece can be measured simply and very accurately.

Consequently, the total amount of antigens or antibodies can be measured precisely.

The measuring device for immunochromatography test pieces according to the present invention may be further characterized in that the irradiation optical system and the detection optical system are disposed in such a manner that the imaging element receives the reflected light of the measurement light irradiated onto the immunochromatography test piece; and the reflectivity of the color pattern is measured on the basis of the reflected light received by the imaging element.

The degree of coloration of the immunochromatography test piece can be measured simply and very accurately. Consequently, the total amount of antigens or antibodies can be measured precisely.

BEST MODES FOR CARRYING OUT THE INVENTION

A measuring device for immunochromatography test pieces relating to an embodiment of the present invention is now described with reference to the drawings. In the respective drawings, similar elements or elements having similar functions are similarly labelled, and duplicated description thereof is omitted.

(First Embodiment)

Figure 1:
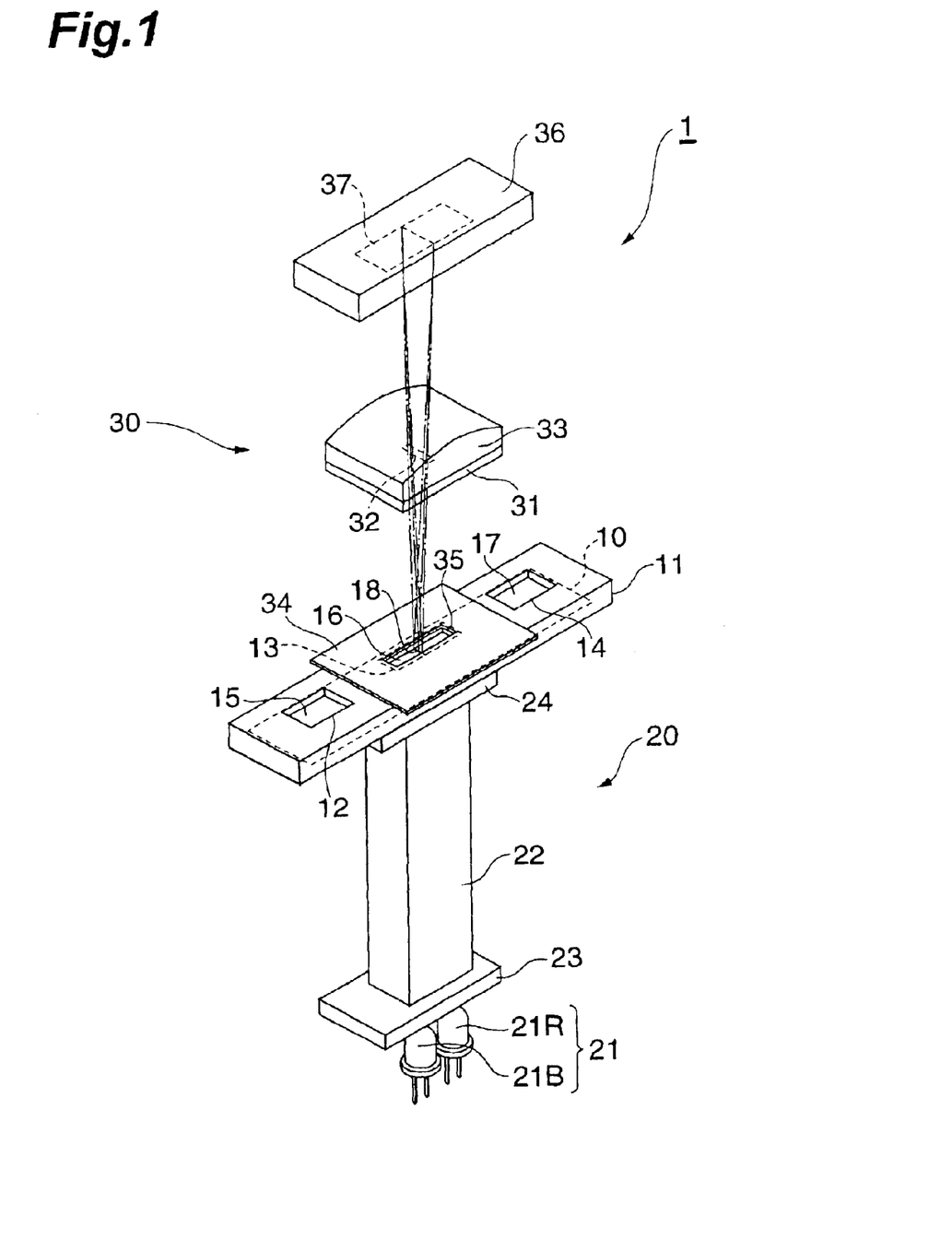
FIG. 1 is an approximate compositional view showing a measuring device for immunochromatography test pieces relating to a first embodiment of the present invention.

Firstly, a measuring device 1 for immunochromatography test pieces relating to a first embodiment is described with reference to FIG. 1.

The measuring device 1 comprises an irradiating optical system 20 for irradiating measurement light onto an immunochromatography test piece 10, and a detection optical system 30 for detecting light from an immunochromatography test piece 10 by irradiation of the measurement light.

The irradiation optical system 20 comprises a light-emitting element 21 and a mixing rod 22. Moreover, the detection optical system 30 comprises an aperture 31, a cylindrical lens 33 forming an imaging lens, and a CCD image sensor 36 forming an imaging element.

The immunochromatography test piece 10 has a long rectangular shape and is made from a material such as a nitrocellulose membrane, or filter paper, or the like. This immunochromatography test piece 10 is held inside a casing 11 having a long rectangular shape in plan view, and a subject application window 12, observation window 13 and control window 14 are provided extending in the direction of the longer side in the casing 11. The immunochromatography test piece 10 comprises a subject application section 15 provided in a position corresponding to the subject application window 12, and detecting sections 16, 17 provided in positions corresponding to the observation window 13 and control window 14. The detecting section 16 has a line shape (or band shape) formed by coating respective antigens (or antibodies) which react with antigens (or antibodies) in the subject, and causing same to solidify. The casing 11 which holds the immunochromatography test piece 10 is held by holding means (not illustrated). The observation window 13 has a size of 4 mm×8 mm, for example.

The subject is applied dropwise via the subject application window 12 onto the subject application section 15 of the immunochromatography test piece 10. The antigens (or antibodies) in the subject couple with the indicator dye and the indicator dye coupled with the antigens (or antibodies) in the subject, as well as unreacted indicator dye, travel in the longitudinal direction of the immunochromatography test piece 10. Supposing that the subject contains antigens, then it is assumed that the antigens will undergo an antigen/antibody reaction with the respective detecting sections. As the subject travels, the antigens in the subject and the antigens fixed to the detecting section 16 react specifically and a line-shaped pattern 18 colored by the indicator dye is formed in the detecting section 16 where reaction has taken place. This colored line-shaped pattern 18 is formed extending in a direction intersecting (for example, orthogonally) with the direction of travel of the antigens (or antibodies) of the subject in the immunochromatography test piece 10, and it can be observed by means of the observation window 13.

The light-emitting element 21 comprises a plurality of LEDs having different light emission wavelengths, in the present embodiment, a blue LED 21B and a red LED 21R. If the line-shaped pattern 18 formed by the antigen/antibody reaction is colored red, then the blue LED 21B is caused to emit light. If the line-shaped pattern 18 formed by the antigen/antibody reaction is colored blue, then the red LED 21R is caused to emit light.

The mixing rod 22 is a square-shaped (or circular-shaped) rod made from transparent acrylic resin for mixing the light output by the light-emitting element 21 (blue LED 21B or red LED 21R), and it has a light input face and a light output face at the respective ends thereof. The aforementioned light-emitting element 21 is positioned on the light input face side of the mixing rod 22. An immunochromatography test piece 10 (casing 11) is positioned on the light output face side of the mixing rod 22. More specifically, the immunochromatography test piece 10 (casing 11) is positioned opposing the light output face of the mixing rod 22 in such a manner that the observation window 13 of the casing 11 coincides with the light output face of the mixing rod 22. The light output face of the mixing rod 22 has a size of 8 mm×14 mm, and the surface area of the light output face of this mixing rod 22 is set to a larger area than the surface area of the opening in the observation window 13 of the casing 11.

Diffusion plates 23, 24 forming diffusing means are provided at the light input face and light output face of the mixing rod 22, in a state of contact with the light input face and light output face of the mixing rod 22. These diffusing plates 23, 24 are made from opaque acrylic resin. Instead of providing diffusing plates 23, 24, it is also possible to form the actual light input face and light output face of the mixing rod 22 into ground glass surfaces in order to provide diffusing means.

The light output from the light-emitting element 21 (blue LED 21B or red LED 21R) is diffused by the diffusing plate 23 and then enters into the mixing rod 22 via the light input face of the mixing rod 22. The light that has entered the mixing rod 22 is mixed by being fully reflected at the side faces of the mixing rod 22 whilst it is propagated therein, and this mixed light arrives at the light output face of the mixing rod 22. The light arriving at the light output face of the mixing rod 22 is diffused by the diffusing plate 24, and is then irradiated as measurement light from the rear face of the observation window 13 of the casing 11 in the direction of the immunochromatography test piece 10 (observation window 13 of the casing 11).

The cylindrical lens 33 is positioned in such a manner that the direction of the generating line of the curved face of the cylindrical lens 33 intersects (for example, orthogonally) with the direction of travel of the antigens (or antibodies) of the subject in the immunochromatography test piece 10, in other words, in such a manner that it is facing in the direction of extension of the line-shaped pattern 18 formed by coloration of the immunochromatography test piece 10. The cylindrical lens 33 forms an image of the line-shaped pattern 18 formed in the immunochromatography test piece 10, by means of the input transmitted light from the immunochromatography test piece 10 (casing 11).

The aperture 31 is positioned on the light input face side of the cylindrical lens 33. A long rectangular-shaped slit 32 extending in the direction of the generating line of the curved face of the cylindrical lens 33 is formed in the aperture 31. The slit 32 in the aperture 31 restricts the transmitted light which passes through the immunochromatography test piece 10 (casing 11) upon irradiation of measurement light and is emitted via the observation window 13.

An aperture 34 for restricting light other the light from the observation window 13 from being input to the cylindrical lens 33 is provided on the light output face of the immunochromatography test piece 10 (casing 11). A hole section 35 for passing the transmitted light from the immunochromatography test piece 10 (casing 11) is provided in the aperture 34.

The CCD image sensor 36 has a light receiving face 37, which is situated at the position where an image of the transmitted light from the immunochromatography test piece 10 (casing 11) is formed by the cylindrical lens 33. Light-receiving elements are provided in a one-dimensional or two-dimensional array on the light-receiving face 37. The CCD image sensor 36 detects the transmitted light from the immunochromatography test piece 10 by capturing the image formed by the cylindrical lens 33 on the light receiving face 37.

Figure 2:
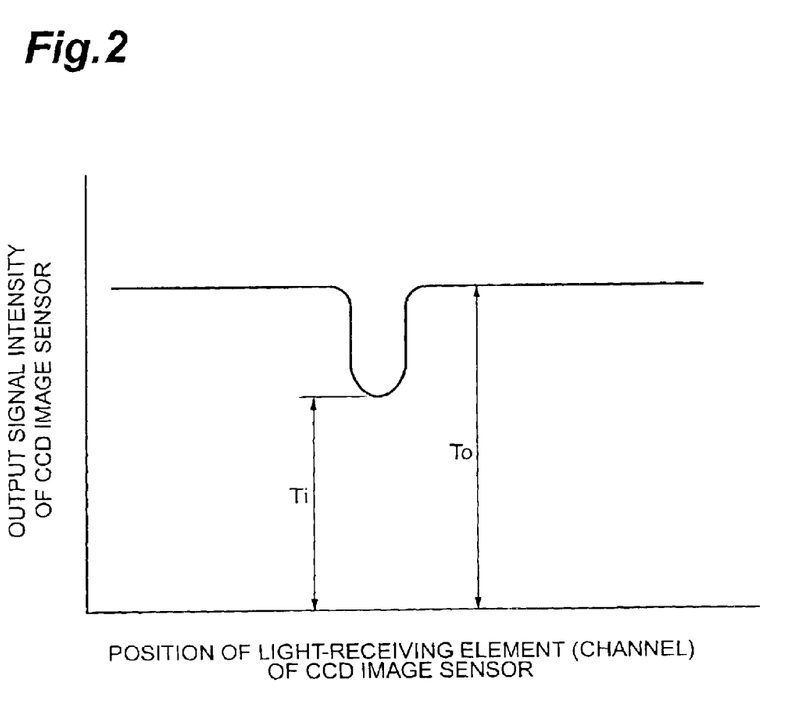
FIG. 2 is a graph showing the light absorption profile of light transmitted by an immunochromatography test piece.

Next, a method for determining the concentration of the subject is described. When transmitted light from the immunochromatography test piece 10 is detected by the CCD image sensor 36, the light absorption of the line-shaped pattern 18 formed by coloration is determined as described below, on the basis of the output signal from the CCD image sensor 36. Firstly, a light absorption profile of the transmitted light of the immunochromatography test piece 10 is created as illustrated in FIG. 2, on the basis of the output signal intensity from the CCD image sensor 36 and the position of the light-receiving element (channel) of the CCD image sensor 36. Thereupon, the light absorption ABS is calculated by means of the following equation (1), taking $T_o$ as the output signal intensity at a position in the created absorption profile corresponding to a portion of the immunochromatography test piece 10 that is not colored, and taking $T_i$ as the output light intensity at a position corresponding to a colored region thereof (line-shaped pattern 18).

$$ABS = \log(T_o/T_i) \tag{1}$$

When the light absorption ABS is calculated, the total quantity (concentration) of antibodies or antigens contained in the subjected is derived from the light absorption ABS, by referring to a previously created quantity characteristics graph.

It is also possible to calculate the light absorption ABS on the basis of the following equation (2), taking $T_{ao}$ as the average output signal intensity at a position of the created absorption profile corresponding to a region of the immunochromatography test piece that is not colored, and $T_{ai}$ as the average output signal intensity at a position corresponding to a color region (line-shaped pattern).

$$ABS = \log(T_{ao}/T_{ai}) \tag{2}$$

In this way, an irradiation optical system 20 and a detection optical system 30 are provided in the measuring device 1. The irradiation optical system 20 comprises a light-emitting element 21 (blue LED 21B or red LED 21R), and a mixing rod 22, and the light emitted from the mixing rod 22 is irradiated as measurement light onto the immunochromatography test piece 10 (casing 11). The detection optical system 30 comprises a cylindrical lens 33 and CCD image sensor 36, and detects transmitted light from the immunochromatography test piece 10 (casing 11) by means of the CCD image sensor 36. Since the light output by the light-emitting elements 21 is mixed by the mixing rod 22 before being irradiated onto the immunochromatography test piece 10 (casing 11), attenuation of the light from the light-emitting elements 21 is suppressed, and the amount of light irradiated onto the immunochromatography test piece 10 is increased. Consequently, the CCD image sensor 36 is able reliably to detect a line-shaped pattern 18 formed by coloration of the immunochromatography test piece 10. Moreover, since light-emitting elements 21 (a blue LED 21B and a red LED 21R) are used, it is possible to suppress increase in the size of the measuring device 1.

Furthermore, in the measuring device 1, since diffusing plates 23, 24 are provided at the light input face and light output face of the mixing rod 22, the light irradiated onto the immunochromatography test piece 10 (casing 11) is approximately equalized. Thereby, it is possible to perform detection of the line-shaped pattern 18 in the immunochromatography test piece 10 by means of the CCD image sensor 36 with even greater reliability.

Furthermore, in the measuring device 1, since the surface area of the light output face of the mixing rod 22 is greater than the surface area of the observation window 13 of the casing 11, the light irradiated onto a position corresponding to the observation window 13 of the immunochromatography test piece 10 will be further equalized. Thereby, the detection of the line-shaped pattern 18 in the immunochromatography test piece 10 by means of the CCD image sensor 36 can be performed with even greater reliability.

Moreover, the measuring device 1 has a cylindrical lens 33 forming an imaging lens, this cylindrical lens 33 being provided in such a manner that the direction of the generating line of the curved face thereof intersects with the direction of travel of the antigens or antibodies in the immunochromatography test piece 10, and due to irradiation of measurement light, an image of the line-shaped pattern 18 formed in a direction intersecting with the direction of travel of the antigens or antibodies is formed on the CCD image sensor 36. Thereby, light which is parallel to the direction of travel of the antigens or antibodies in the immunochromatography test piece 10 is formed as an image on the CCD image sensor 36, and light which is orthogonal to the direction of travel of the antigens or antibodies in the immunochromatography test piece 10 is defocused and equalized. Consequently, even if uneven coloration occurs in the direction of extension of the line-shaped pattern 18 formed by coloration of the immunochromatography test piece 10, the uneven coloration is equalized optically by the cylindrical lens 33, and a pattern wherein the uneven discoloration is equalized optically is formed as an image on the CCD image sensor 36. As a result, the degree of coloration of the line-shaped pattern 18 formed in the immunochromatography test piece 10 can be measured with good accuracy.

Furthermore, in the measuring device 1, since the aperture 31 formed with a long rectangular-shaped slit 32 extending in the direction of the generating line of the curved face of the cylindrical lens 33 is disposed on the light input face side of the cylindrical lens 33, it is possible to focus an image having little aberration on the CCD image sensor 36.

Moreover, the irradiation optical system 20 and detection optical system 30 in the measuring device 1 are positioned in such a manner that the CCD image sensor 36 receives the transmitted light of the measurement light irradiated onto the immunochromatography test piece 10, and the light absorption of the line-shaped pattern 18 formed by coloration is measured on the basis of the transmitted light received by the CCD image sensor 36. Thereby, the degree of coloration of the line-shaped pattern 18 formed in the immunochromatography test piece 10 can be measured simply and very accurately, and the total amount (concentration) of antigens or antibodies contained in the subject can be measured precisely.

(Second Embodiment)

Next, the measuring device 101 for an immunochromatography test piece relating to a second embodiment is described with reference to FIGS. 3 to 8. The measuring device 101 relating to the second embodiment differs from the measuring device 1 relating to the first embodiment in that the light path is constituted in a bent fashion by using mirrors.

Figure 3:
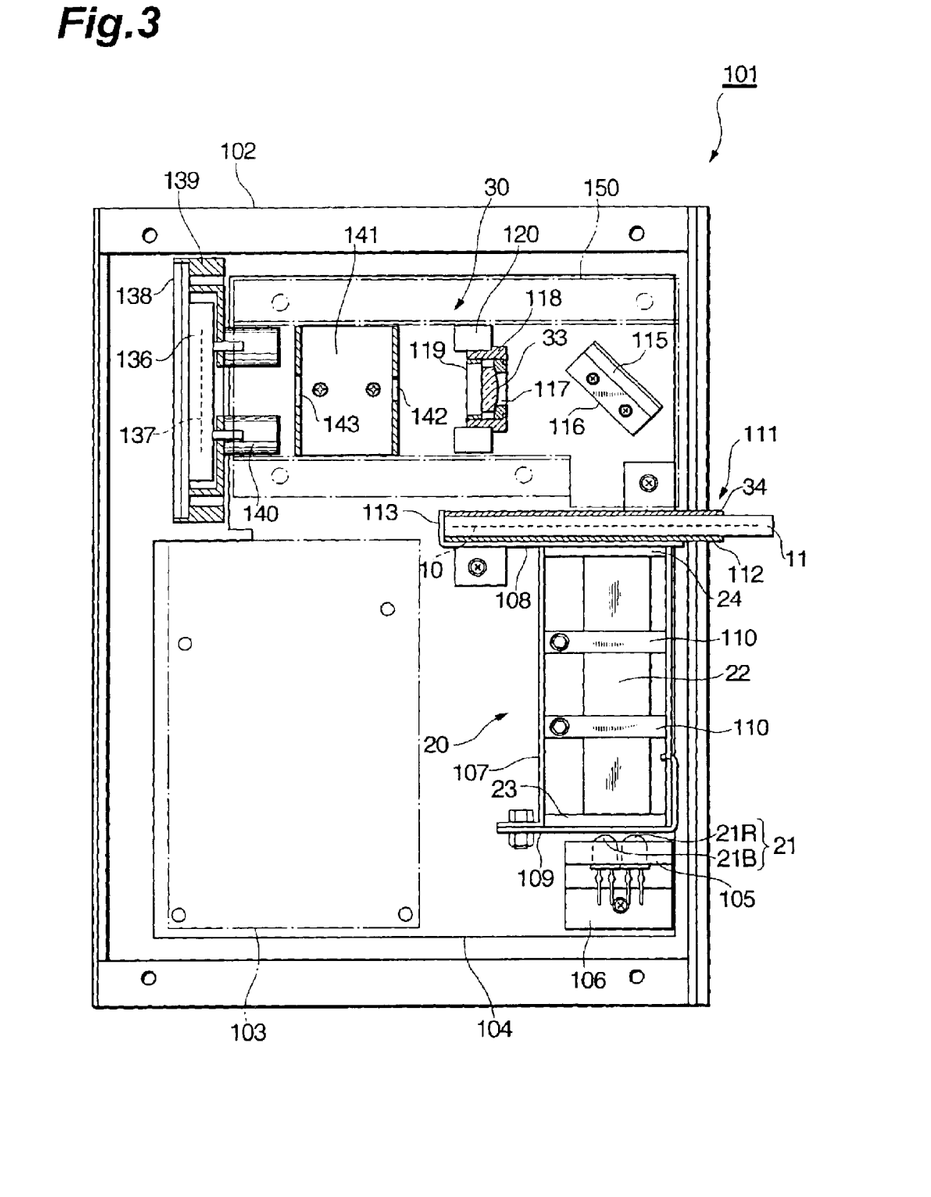
FIG. 3 is a side view of a measuring device for immunochromatography test pieces relating to a second embodiment of the present invention.
Figure 4:
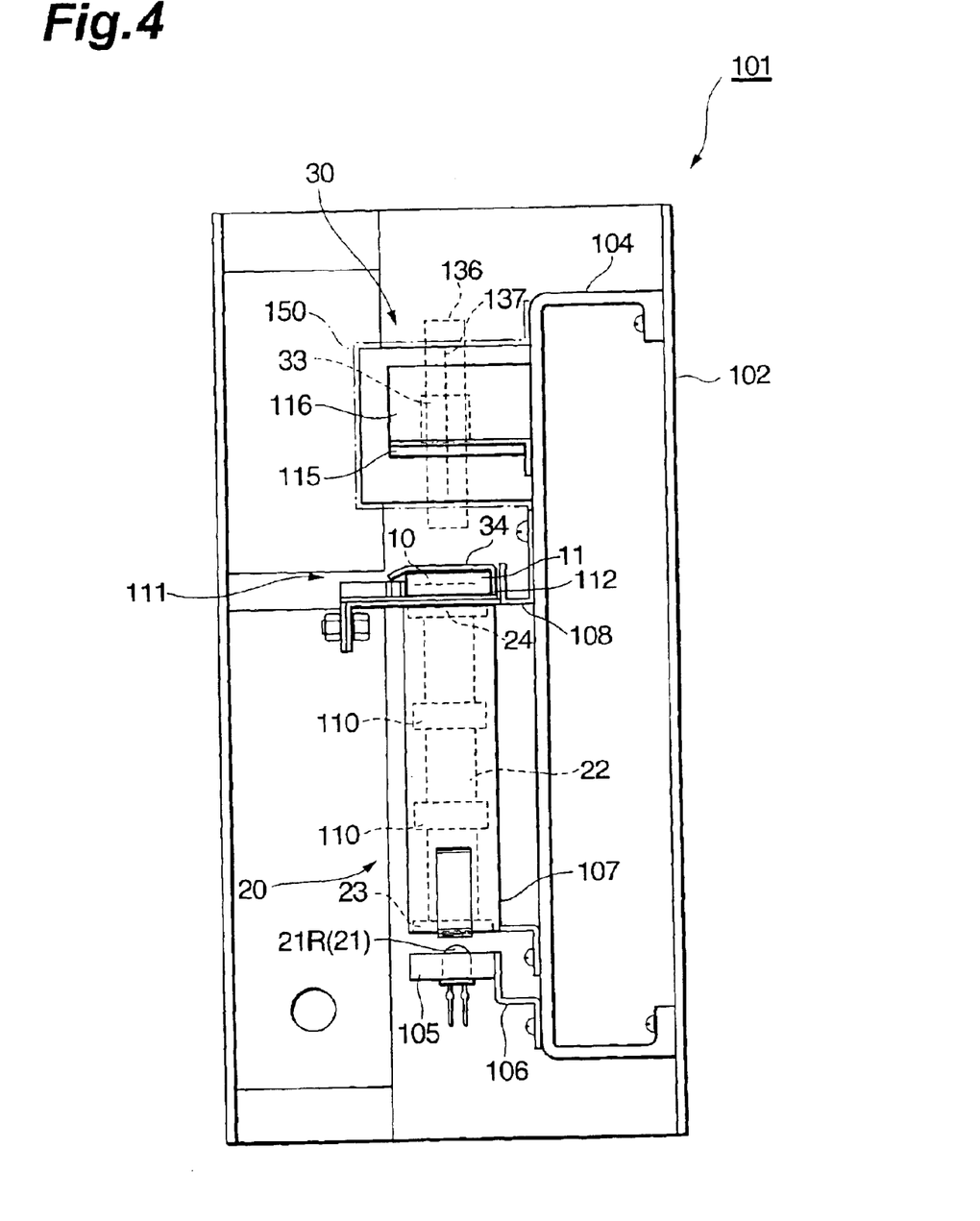
FIG. 4 is a front view of a measuring device for immunochromatography test pieces relating to a second embodiment of the present invention.

As shown in FIG. 3 and FIG. 4, the measuring device 101 comprises a case 102, and a lid (not illustrated) which fits onto the case 102. A chassis 104 is fitted inside the case 102 in order to position an irradiation optical system 20, a detection optical system 30, and a control circuit 103 for controlling the operation of the measuring device 101 by performing various calculation processes.

The light-emitting elements 21 (blue LED 21B or red LED 21R) are fixed to an installation plate 105, and this installation plate 105 is attached to the chassis 104 via a bracket 106.

A mixing rod 22 is situated inside a rod case 107, in a state whereby the light input face and light output face of the mixing rod 22 contact diffusion plates 23, 24. The position of the mixing rod 22 in the direction of the light guide is limited by means of a restricting section 108 formed integrally with the rod case 107 confronting the diffusion plate 24, and a rod pressing plate 109 combined with the rod case 107 confronting the diffusion plate 23. A plurality of rod holders 110 are installed on the side face of the mixing rod 22, at prescribed intervals in the light guide direction of the mixing rod 22. The position of the mixing rod 22 in the direction orthogonal to the light guide direction thereof is limited by means of these rod holders 110 confronting the side walls of the rod case 107.

A test piece holder 111 constituted so that an immunochromatography test piece 10 (casing 11) can be inserted therein, is provided on the upper face of the restricting section 108 (rear side of the face confronting the diffusion plate 24). This test piece holder 111 functions as holding means for holding the immunochromatography test piece 10 (casing 11).

The test piece holder 111 is constituted in such a manner that, the casing 11 makes contact with the aperture 34, when it is inserted inside the test piece holder 111 and positioned in a test piece installation section 112 formed integrally with the aperture 34. The test piece holder 111 is installed on the chassis 104 in a state where the restricting section 108 and test piece installation section 112 are in mutual contact. The insertion position of the immunochromatography test piece 10 (casing 11) in the longitudinal direction is restricted by means of a restricting section 113 formed integrally with the rod case 107 (restricting section 108) making contact with the end of the casing 11 in the longitudinal direction thereof.

Figure 5:
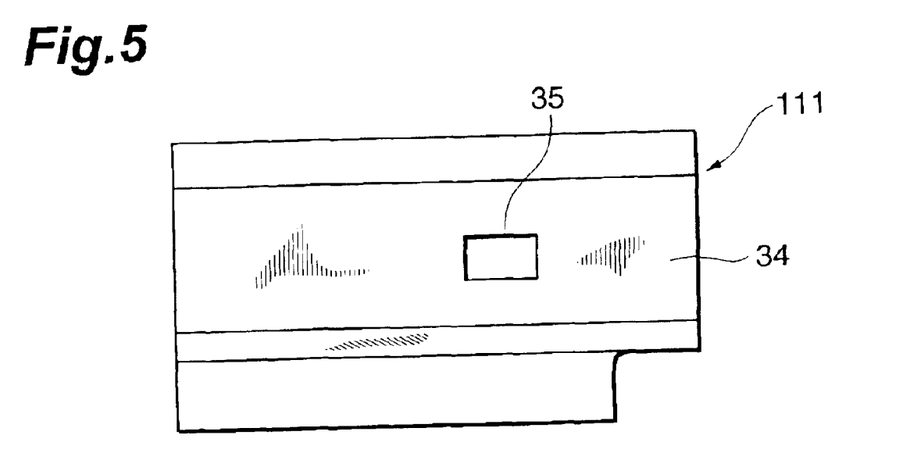
FIG. 5 is a plan view of a test piece holder included in a measuring device for immunochromatography test pieces relating to a second embodiment of the present invention.
Figure 6:
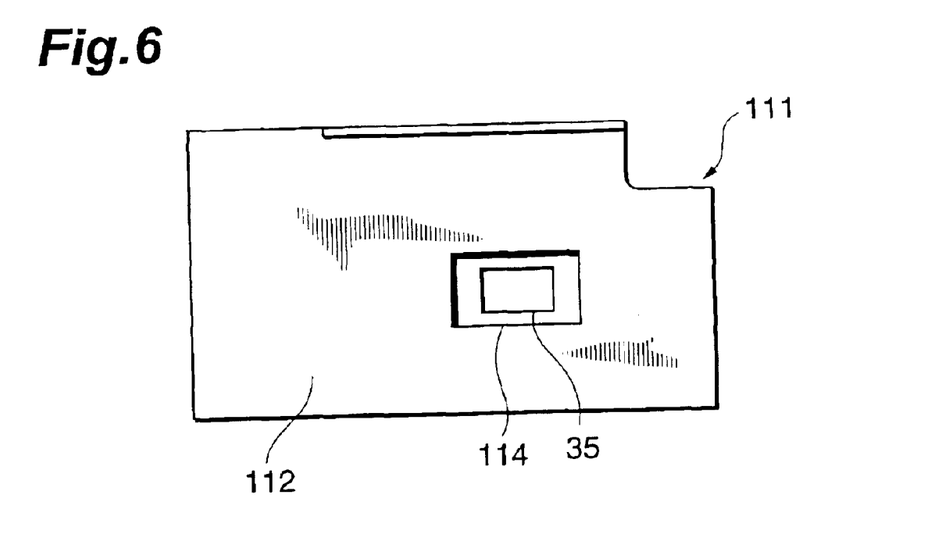
FIG. 6 is a rear view of a test piece holder included in a measuring device for immunochromatography test pieces relating to a second embodiment of the present invention.

As shown in FIG. 5, a hole section 35 for passing transmitted light from the immunochromatography test piece 10 (casing 11) is provided in the aperture 34. The hole section 35 of the aperture 34 has a size of 5 mm×8 mm. Furthermore, as shown in FIG. 6, a hole section 214 for irradiating light from the diffusion plate 24 onto the immunochromatography test piece 10 (casing 11) is provided on the test piece installation section 112 of the test piece holder 111. The hole section 114 of the test piece installation section 112 has a size of 8 mm×14 mm. The light output face of the mixing rod 22 also has a size of 8 mm×14 mm. The observation window has a size of 4 mm×8 mm.

A mirror 115 is provided on top of the test piece holder 111. This mirror 115 is installed on the chassis 104 via a mirror holder 116. The light reflected by the mirror 115 is input to the cylindrical lens 33. The light path is bent in the measuring device 101 by means of this mirror 115, and as illustrated in FIG. 3, the irradiation optical system 20 and the detection optical system 30 are located in an inverse L shape. The control circuit 103 is installed on the chassis 104 in a position to the inner side of the irradiation optical system 20 and detection optical system 30 provided in an inverse L shape. By laying out the irradiation optical system 20, detection optical system 30 and control circuit 103 in this way, it is possible to achieve compactification of the measuring device 101.

Figure 7:
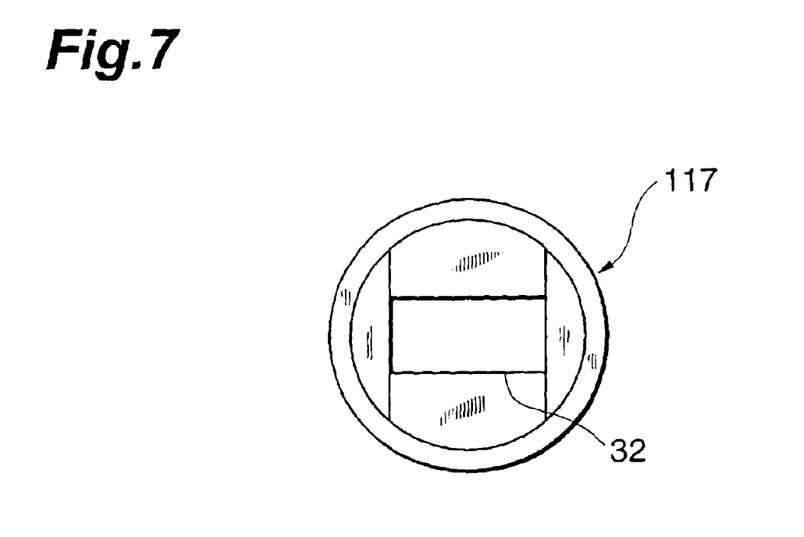
FIG. 7 is a plan view of a lens mask included in a measuring device for immunochromatography test pieces relating to a second embodiment of the present invention.

The cylindrical lens 33 is positioned in such a manner that the direction of the generating line of the curved face of the cylindrical lens 33 intersects (orthogonally, for example,) with the direction of travel of the antigens (or antibodies) of the subject in the immunochromatography test piece 10, in other words, in such a manner that it faces in the direction of extension of the line-shaped pattern 18 formed by coloration in the immunochromatography test piece 10. A lens mask 117 forming an aperture is positioned on the light input side of the cylindrical lens 33. As shown in FIG. 7, a long rectangular slit 32 extending in the direction of the generating line of the curved face of the cylindrical lens 33 is formed in the lens mask 117. The size of this slit 32 is set to 4 mm×8 mm.

The cylindrical lens 33 and lens mask 117 are held on either side by a lens holder 118 and pressing ring 119, by means of the lens holder 118 and pressing ring 119 being screw fitted together. The lens holder 118 is fixed in a state where it is inserted into a hole section of a lens installation tube 120. The lens installation tube 120 with the lens holder 118 fixed thereto is installed on the chassis 104.

Figure 8:
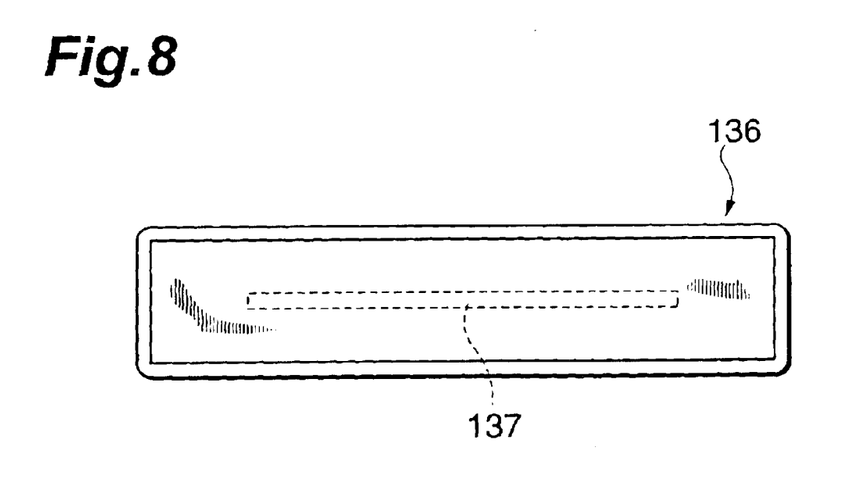
FIG. 8 is a plan view of a linear array CCD image sensor included in a measuring device for immunochromatography test pieces relating to a second embodiment.

Light exiting the cylindrical lens 33 is incident on a linear array CCD image sensor 136. The linear array CCD image sensor 136 has a light receiving face 137 extending in a one-dimensional direction, as illustrated in FIG. 8. The linear array CCD image sensor 136 is disposed in such a manner that the light receiving face 137 thereof is positioned at the point where the transmitted light from the immunochromatography test piece 10 (casing 11) is formed into an image by the cylindrical lens 33. A plurality of light-receiving elements (in the present embodiment, 2048 elements) are disposed in a one-dimensional fashion on the light receiving face 137 of the linear array CCD image sensor 136. The linear array CCD image sensor 136 is fixed to a sensor holder 139 by means of a substrate 138, and this sensor holder 139 is attached to the chassis 104 via a sensor installation tube 140. As shown in FIG. 3, the direction of extension of the light receiving face 137 of the linear array CCD image sensor 136 is a direction which intersects with the direction of the generating line of the curved face of the cylindrical lens 33, when the linear array CCD image sensor 136 is installed in the chassis 104.

A baffle plate 141 for eliminating stray light is provided between the cylindrical lens 33 and the linear array CCD image sensor 136. Hole sections 142, 143 for transmitting light exiting from the cylindrical lens 33 are formed in this baffle plate 141. The baffle plate 141 is installed on the chassis 104.

The detection optical system from the aperture 34 to the linear array CCD image sensor 136 is covered by a light shielding tube 150 in order to optically shield this detection optical system. The light shielding tube 150 is installed on the chassis 104.

The measuring device 101 having the foregoing composition provides the same action and beneficial effects as the measuring device 1 relating to the first embodiment and is able reliably to detect a line-shaped pattern 18 formed by coloration of an immunochromatography test piece 10, by means of the linear array CCD image sensor 136. Moreover, since light-emitting elements 21 (blue LED 21B or red LED 21R) are used as light sources, it is possible to prevent increase in the size of the measuring device 101.

Furthermore, the measuring device 101 has a cylindrical lens 33 as an imaging lens, and this cylindrical lens 33 is disposed so that the direction of the generating line of the curved face thereof intersects with the direction of travel of the antigens or antibodies in the immunochromatography test piece 10, and it forms an image of the line-shaped pattern 18 formed in a direction intersecting with the direction of travel of the antigens or antibodies, on the linear array CCD image sensor 136, due to irradiation of measurement light. Thereby, light that is parallel to the direction of travel of the antigens or antibodies in the immunochromatography test piece 10 is formed as an image on the linear array CCD image sensor 136, and light that is orthogonal to the direction of travel of the antigens or antibodies in the immunochromatography test piece 10 is defocused and equalized. Consequently, even if uneven coloration occurs in the direction of extension of the line-shaped pattern 18 formed by coloration of the immunochromatography test piece 10, this uneven coloration will be optically equalized by the cylindrical lens 33, and hence a pattern wherein uneven coloration is optically equalized will be formed as an image on the linear array CCD image sensor 136. As a result, it is possible to measure the degree of coloration of the line-shaped pattern 18 formed on the immunochromatography test piece 10 to a high level of accuracy.

Moreover, in the measuring device 101, since a lens mask 117 formed with a long rectangular slit 32 extending in the direction of the generating line of the curved face of the cylindrical lens 33 is provided at the light input face of the cylindrical lens 33, it is possible to form an image having little aberration on the linear array CCD image sensor 136.

Moreover, in the measuring device 101, since a linear array CCD image sensor 136 is used as an imaging element, a measuring device 101 having an inexpensive and compact composition can be achieved. As described above, since any unevenness in coloration is optically equalized by the cylindrical lens 33, it is possible to measure the degree of coloration of the line-shaped pattern 18 formed in the immunochromatography test piece 10 with a high level of accuracy, even if a linear array CCD image sensor 136 is used as an imaging element.

(Third Embodiment)

Figure 9:
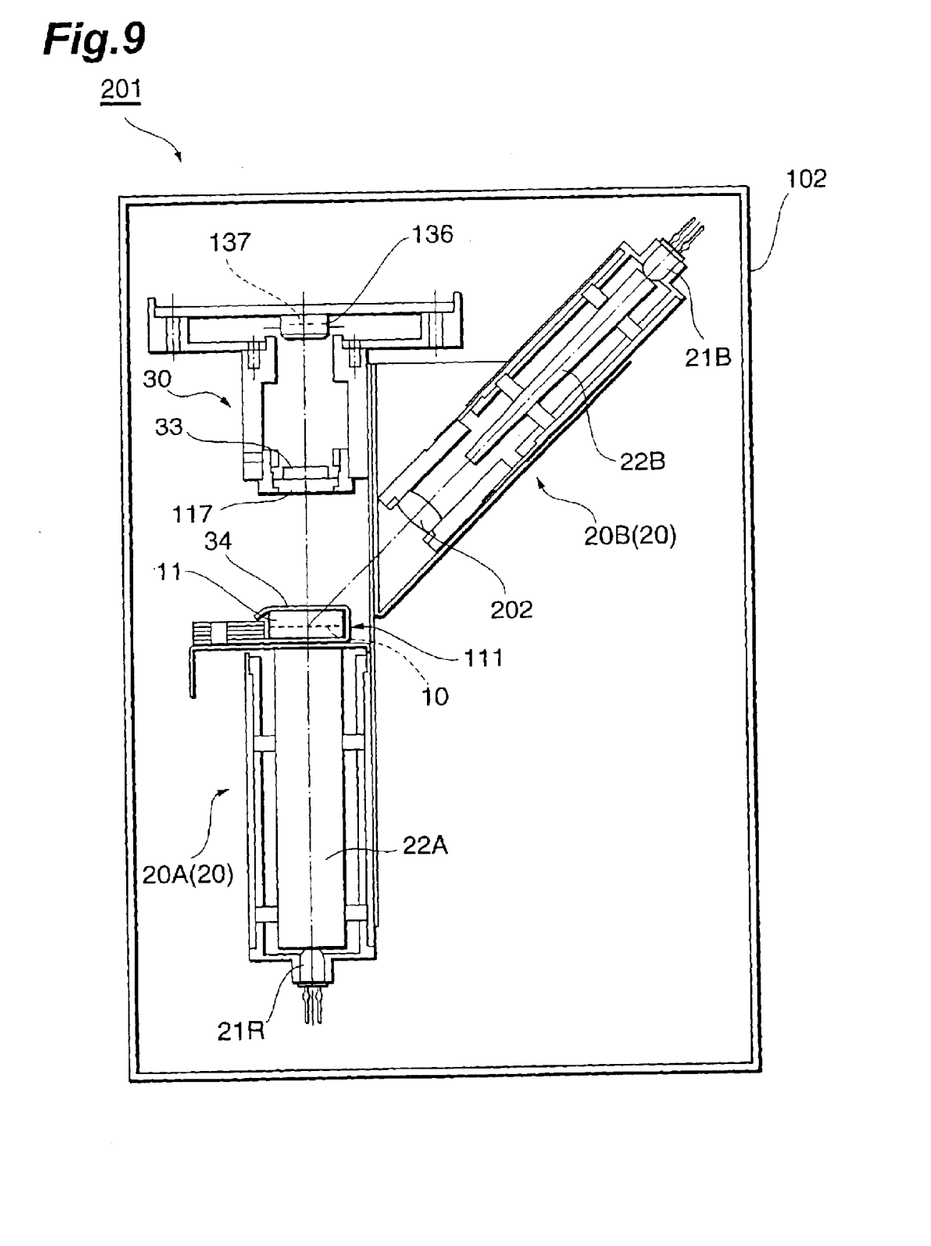
FIG. 9 is a compositional view of a measuring device for immunochromatography test pieces relating to a third embodiment of the present invention.
Figure 10:
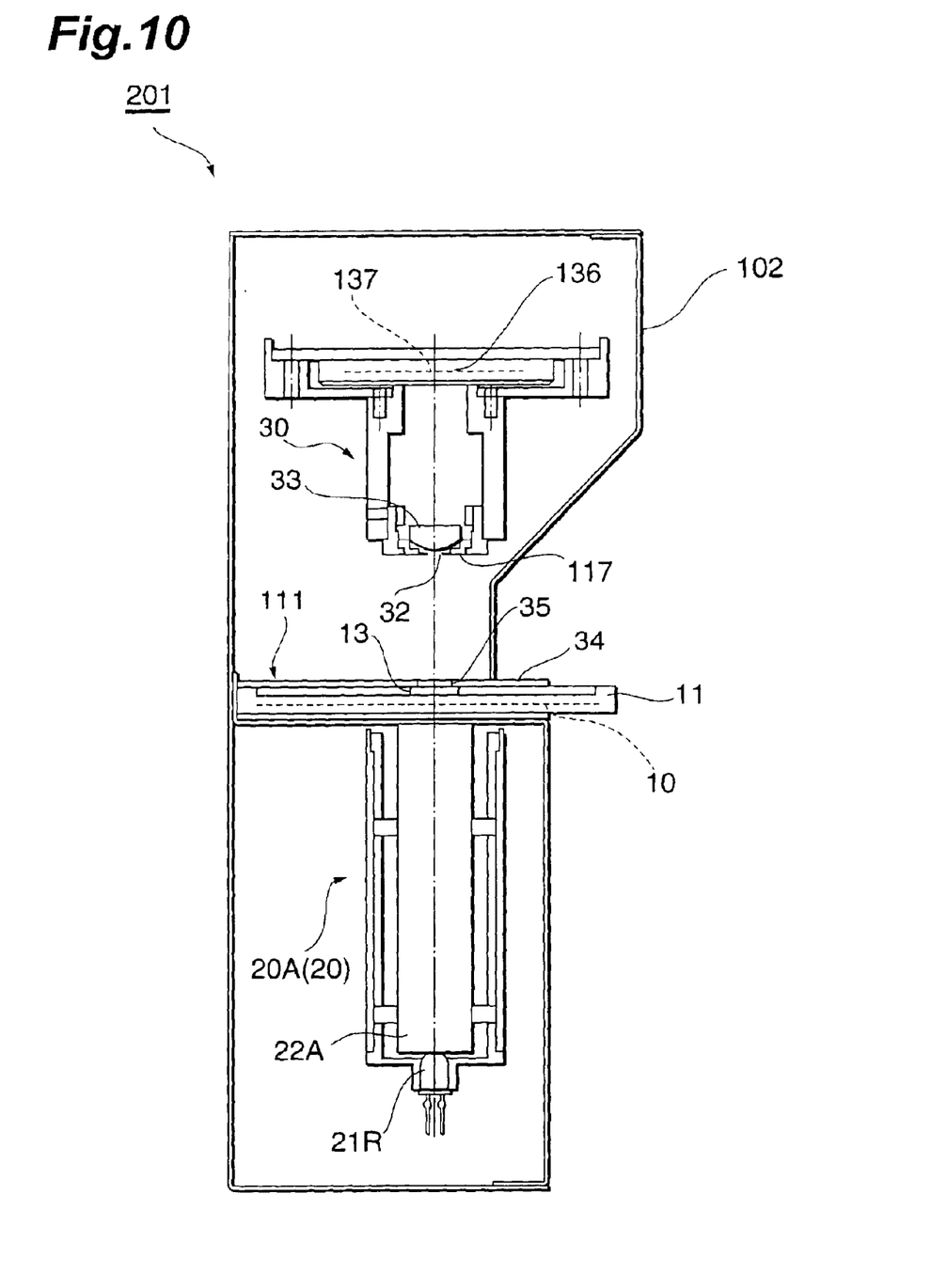
FIG. 10 is a compositional view of a measuring device for immunochromatography test pieces relating to a third embodiment of the present invention.

Next, a measuring device 201 for immunochromatography test pieces relating to a third embodiment is described on the basis of FIG. 9 to FIG. 10. The measuring device 201 relating to the third embodiment differs from the measuring devices 1, 101 relating to the first embodiment and second embodiment in that the transmitted light and the reflected light of the measurement light irradiated onto an immunochromatography test piece are detected by the imaging element.

In the measuring device 201, the irradiation optical system 20 comprises a first irradiation optical system 20A for irradiating measurement light from the rear side of an immunochromatography test piece 10 (casing 11), and a second irradiation optical system 20B for irradiating measurement light from the front side of an immunochromatography test piece 10 (casing 11). The immunochromatography test piece 10 (casing 11) is held in a test piece holder 111 forming holding means.

The first irradiation optical system 20A comprises, as a light-emitting element, a red LED 21R (or blue LED 21B), and a first mixing rod 22A. The light input face and light output face of a first mixing rod 22A are processed to ground glass faces.

Light output from the red LED 21R (or blue LED 21B) is diffused by the ground glass face of the light input face of the first mixing rod 22A, and enters into the first mixing rod 22A. The light that has entered into the first mixing rod 22A is mixed by total reflection at the side faces of the first mixing rod 22A as it propagates therein, and it is diffused and output from the light output face of the first mixing rod 22A. The light exiting the first mixing rod 22A is irradiated onto the immunochromatography test piece 10 (observation window 13 of casing 11) as measurement light, from the rear side of the observation window 13 of the casing 11.

The second irradiation optical system 20B comprises a blue LED 21B (or red LED 21R) as a light-emitting element, a second mixing rod 22B, and a condensing lens 202. The light input face and light output face of the second mixing rod 22B are processed to ground glass faces, similarly to the first mixing rod 22A.

Light emitted by the blue LED 21B (or red LED 21R) is diffused by the ground glass face of the light input face of the first mixing rod 22B, and enters into the second mixing rod 22B. The light that has entered into the second mixing rod 22B is mixed by total reflection at the side faces of the second mixing rod 22B as it propagates therein, and it is diffused and output from the light output face of the second mixing rod 22B. The light exiting the second mixing rod 22B is condensed by the condensing lens 202, and is then irradiated onto the immunochromatography test piece 10 (observation window 13 of casing 11) as measurement light, via the observation window 13 of the casing 11.

The measurement light irradiated from the first irradiation optical system 20A is received and detected as transmitted light from the immunochromatography test piece 10 (casing 11) by the linear array CCD image sensor 136. Furthermore, the measurement light irradiated from the second irradiation optical system 20B is received as detected as reflected light from the immunochromatography test piece 10 (casing 11) by the linear array CCD image sensor 136.

A cylindrical lens 33 is positioned in such a manner that the direction of the generating line of the curved face of the cylindrical lens 33 intersects (orthogonally, for example,) with the direction of travel of the antigens (or antibodies) of the subject in the immunochromatography test piece 10, in other words, in such a manner that it faces in the direction of extension of the line-shaped pattern 18 formed by coloration in the immunochromatography test piece 10. A lens mask 117 formed with a long rectangular slit 32 extending in the direction of the generating line of the curved face of the cylindrical lens 33 is disposed at the light input face of the cylindrical lens 33. The linear array CCD image sensor 136 is disposed in such a manner that the direction of extension of the light receiving face 137 of the linear array CCD image sensor 136 intersects (orthogonally, for example) with the direction of the generating line of the curved face of the cylindrical lens 33.

The measuring device 201 having the foregoing composition provides the same action and beneficial effects as the measuring devices 1, 101 relating to the first embodiment and second embodiment, and is able reliably to detect a line-shaped pattern 18 formed by coloration of an immunochromatography test piece 10, by means of the linear array CCD image sensor 136. Moreover, since light-emitting elements 21 (blue LED 21B or red LED 21R) are used as light sources, it is possible to prevent increase in the size of the measuring device 201.

Furthermore, the measuring device 201 has a cylindrical lens 33 as an imaging lens, and this cylindrical lens 33 is disposed so that the direction of the generating line of the curved face thereof intersects with the direction of travel of the antigens or antibodies in the immunochromatography test piece 10. Consequently, even if uneven coloration occurs in the direction of extension of the line-shaped pattern 18 formed by coloration of the immunochromatography test piece 10, this uneven coloration will be optically equalized by the cylindrical lens 33, and hence a pattern wherein uneven coloration is optically equalized will be formed as an image on the linear array CCD image sensor 136. As a result, it is possible to measure the degree of coloration of the line-shaped pattern 18 formed on the immunochromatography test piece 10 to a high level of accuracy.

Moreover, in the measuring device 201, the irradiation optical system 20 and detection optical system 30 are disposed in such a manner that the linear array CCD image sensor 136 receives both transmitted light and reflected light of the measurement light irradiated onto the immunochromatography test piece 10, and the light absorption of the line-shaped pattern 18 formed by coloration is measured on the basis of the transmitted light or reflectivity thus received by the linear array CCD image sensor 136. Accordingly, the degree of coloration of the line-shaped pattern 18 formed on the immunochromatography test piece 10 can be measured simply and very accurately, and hence the total amount (concentration) of antigens or antibodies contained in the subject can be measured precisely.

If the concentration of antigens or antibodies is very low, then the degree of coloration will be low and the amount of detected light is very weak. In cases where the concentration of antigens or antibodies is very low in this way, it is beneficial to use light absorption measurement based on the transmitted light. Moreover, if the concentration of the antigens or antibodies is high and the amount of detected light is high, then measurement of the reflectivity based on the reflected light is performed. As described above, it is possible to measure the concentration of antigens or antibodies, accurately across a wide range, by selective use of transmitted light measurement or reflected light measurement, according to the concentration of the antigens or antibodies.

The present invention is not limited to the foregoing embodiments, and the aforementioned numerical values, and the like, may also be changed appropriately.

Moreover, in the measuring devices 1, 101 relating to the first embodiment and second embodiment, the transmitted light of the measurement light irradiated onto the immunochromatography test piece 10 (casing 11) is received by a CCD image sensor 36, 136, and the light absorption of the line-shaped pattern 18 formed in the immunochromatography test piece 10 is measured on the basis of the transmitted light thus received by the CCD image sensor 36, 136, but the invention is not limited to this. For example, it is also possible for the reflected light of the measurement light irradiated onto the immunochromatography test piece 10 (casing 11) to be received by the CCD image sensor 36, 136, in such a manner that the measuring devices 1, 101 measure the reflectivity of the line-shaped pattern 18 formed in the immunochromatography test piece 10 on the basis of the reflected light thus received by the CCD image sensor 36, 136.

INDUSTRIAL APPLICABILITY

The present invention is applicable to a measuring device for immunochromatography test pieces used in pregnancy examinations, occult blood in faeces examinations, and the like.

What is claimed is:

1. A measuring device for an immunochromatography test piece comprising an irradiation optical system for irradiating measurement light onto said immunochromatography test piece; and a detection optical system for detecting light from said immunochromatography test piece due to said measurement light;

wherein said detection optical system comprises a cylindrical lens and an imaging element;

wherein said cylindrical lens is disposed in such a manner that the direction of a generating line thereof intersects with the direction of travel of antigens or antibodies in said immunochromatography test piece, and creates an image on said imaging element of a pattern formed on said immunochromatography test piece in a direction intersecting with the direction of travel of said antigens or antibodies, due to the irradiation of said measurement light from said irradiation optical system; and wherein a member having a slit formed to extend in the direction of the generating line of said cylindrical lens is further provided between said immunochromatography test piece and said cylindrical lens.

2. The measuring device according to claim 1, wherein said imaging element is a linear image sensor wherein a plurality of light-receiving elements are arrayed in a direction approximately orthogonal to the direction of the generating line of said cylindrical lens.

3. The measuring device according to claim 1, wherein said irradiation optical system and said detection optical system are disposed in such a manner that said imaging element receives the transmitted light of said measurement light irradiated onto said immunochromatography test piece; and the light absorption of said pattern is measured on the basis of said transmitted light received by said imaging element.

4. The measuring device according to claim 1, wherein said irradiation optical system and said detection optical system are disposed in such a maimer that said imaging element receives the reflected light of said measurement light irradiated onto said immunochromatography test piece; and the reflectivity of said pattern is measured on the basis of said reflected light received by said imaging element.

5. The measuring device according to claim 3, wherein said pattern comprises a color pattern.

6. The measuring device according to claim 3, wherein said pattern comprises a line pattern.

7. The measuring device according to claim 4, wherein said pattern comprises a color pattern.

8. The measuring device according to claim 4, wherein said pattern comprises a line pattern.

* * * * *